United States Patent [19]

Mongelli et al.

[11] Patent Number: 5,534,539
[45] Date of Patent: Jul. 9, 1996

[54] BIOLOGICALLY ACTIVE UREIDO DERIVATIVES USEFUL AS ANIT-METASTIC AGENST

[75] Inventors: Nicola Mongelli, Milan; Giovanni Biasoli, Gavirate; Mariangela Mariani, Desio; Francesco Sola, Serengo, all of Italy

[73] Assignee: Farmitalia Carlo Erba S.r.l., Milan, Italy

[21] Appl. No.: 489,621

[22] Filed: Jun. 12, 1995

Related U.S. Application Data

[63] Continuation of Ser. No. 200,381, Feb. 23, 1994, abandoned.

[30] Foreign Application Priority Data

Mar. 5, 1993 [GB] United Kingdom .................. 9304589

[51] Int. Cl.$^6$ ................................................ A61K 31/395
[52] U.S. Cl. ........................................ 514/422; 548/518
[58] Field of Search ............................. 514/422; 548/518

[56] References Cited

U.S. PATENT DOCUMENTS

| | | |
|---|---|---|
| 4,912,199 | 3/1990 | Lown et al. . |
| 5,260,329 | 11/1993 | Mongelli et al. . |
| 5,420,296 | 5/1995 | Mongelli et al. . |

FOREIGN PATENT DOCUMENTS

| | | |
|---|---|---|
| 0183352 | 6/1986 | European Pat. Off. . |
| 0486809 | 5/1992 | European Pat. Off. . |
| 0527042 | 2/1993 | European Pat. Off. . |
| 0583161 | 2/1994 | European Pat. Off. . |
| 91/10649 | 7/1991 | WIPO . |
| 9110649 | 7/1991 | WIPO .................................. 548/518 |

OTHER PUBLICATIONS

Lown et al, J. Med. Chem., vol. 32, pp. 2368–2375 (1989).
Ciomei et al Proc. Am. Assoc. Cancer Res., vol. 32, p. 387 (1991) (Abstract No. 2300).
Franzetti et al, S.I.C. Napoli, Oct. 1991, Abstracts.
Mariani et al, "In Vitro Activity of Novel Sulphonic Derivatives of Distamycin A", International symposium on Angiogenesis, St. Gallen (Switzerland), Mar. 1991, Abstracts.
Sola et al, International Symposium on Angiogenesis, St. Gallen (Switzerland) Mar. 1991, Abstracts, Abstract No. 90.
Drug Design and Recovery, vol. 8, No. 1, 1991, pp. 3–35, D. C. Billington, "Angiogenesis and its Inhibition: Potential New Therapies In Oncollogy and Non–Neoplastic Diseases".
Cancer Research, vol. 52, No. 23, Dec. 1, 1992, pp. 6702–6704, B. Teicher, et al., "Antiangiogenic Agents Potentiate Cytotoxic Cancer Therapies Against Primary and Metastatic Disease".
CA 115(19):207848w Preparation of . . . —methlpyrroles, Mongelli et al., 1991.

Primary Examiner—Joseph K. McKane
Attorney, Agent, or Firm—Oblon, Spivak, McClelland, Maier & Neustadt

[57] ABSTRACT

The invention relates to the use of compounds of formula (I)

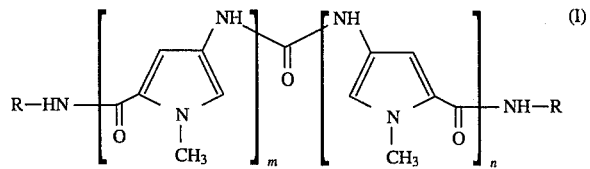

wherein each of m and n, being the same, is an integer of 1 to 3; and each of the R groups, which are the same, is a naphthyl group substituted by 1 to 3 sulfonic groups, or pharmaceutically acceptable salts thereof, in the preparation of a medicament for use in preventing and/or treating the metastatic spread of tumors.

7 Claims, No Drawings

BIOLOGICALLY ACTIVE UREIDO DERIVATIVES USEFUL AS ANIT-METASTIC AGENST

This application is a Continuation of application Ser. No. 08/200,381, filed on Feb. 23, 1994, now abandoned.

The present invention relates to the use of ureido derivatives of substituted pyrroles as antimetastatic agents.

As known, malignancy of cancer is mainly due to metastasis. Because therapy usually fails to destroy multiple secondary tumors, their uncontrolled growth leads to death of patients. Only very few patients die from complications directly arising from the primary tumor. Accordingly, there is a need in therapy of drugs able to prevent and/or block the metastatic spread. WO 91/10649 provides ureido derivatives of poly-4-amino-2-carboxy-1-methyl compounds which have anglogenesis inhibitor activity and have TNF-α neutralizing activity. Accordingly, these prior art compounds can be useful in treating several pathological conditions in mammals where the growth of new blood vessels is detrimental and in which TNF-α is known to play a detrimental role. Now we have found that a selected class of compounds previously disclosed in the above mentioned international application are able to prevent and/or block the metastatic spread of tumors in mammals, including humans.

Accordingly, the present invention provides the use of a compound of formula (I)

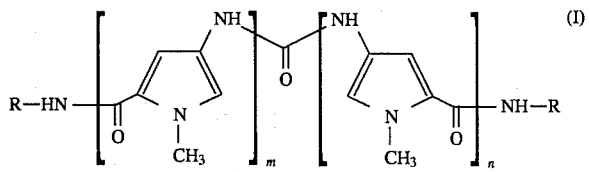

wherein
each of m and n, being the same, is an integer of 1 to 3; and each of the R groups, which are the same, is a naphthyl group substituted by 1 to 3 sulfonic groups, or a pharmaceutically acceptable salt thereof, in the preparation of a medicament for use in preventing and/or treating the metastatic spread of tumors.

The present invention also provides a compound of formula (I), as defined above, or a pharmaceutically acceptable salt thereof, for use in preventing and/or treating the metastatic spread of tumors.

The substituted naphthyl group is preferably a 5-, 6-, 7- or 8-naphthyl group, typically a 7- or 8-naphthyl group. When the naphthyl group is substituted by three sulfonic acid groups, the sulfonic acid substituents are preferably in the 1-, 3- and 5- or 1-, 3- and 6-positions. When it is substituted by 2 acid groups, the sulfonic acid substituents are preferably in the 1- and 3-, 1- and 5-, 3- and 5- or 3- and 6-positions. When it is substituted by one acid group the sulfonic acid substituent is preferably in the 1-, 3- or 5-position. The invention also includes within its scope all the possible isomers, stereoisomers and their mixtures and the metabolites and the metabolic precursors or bioprecursors of the compounds of formula (I).

As already said, the invention includes within its scope also the pharmaceutically acceptable salts of the compounds of formula (I).

Examples of pharmaceutically acceptable salts are either those with inorganic bases, such as sodium, potassium, calcium and aluminium hydroxides, or with organic bases, such as lysine, arginine, N-methyl-glucamine, triethylamine, triethanolamine, dibenzylamine, methylbenzylamine, di-(2-ethyl-hexyl)-amine, piperidine, N-ethylpiperidine, N,N-diethylaminoethylamine, N-ethylmorpholine, β-phenethylamine,N-benzyl-β-phenethylamine, N-benzyl-N,N-dimethylamine and other acceptable organic amines. Sodium and potassium salts are preferred. As stated above, the present invention also includes within its scope pharmaceutically acceptable bioprecursors (otherwise known as pro-drugs) of the compounds of formula (I), i.e. compounds which have a different formula to formula (I) above but which nevertheless upon administration to a human being are converted directly or indirectly in vivo into a compound of formula (I).

Preferred compounds of formula (I) are the compounds wherein m and n are each 2 and each of the R groups is as defined above, and the pharmaceutically acceptable salts thereof.

Examples of specific preferred compounds are:

7,7'-(carbonyl-bis(imino-N-methyl-4,2-pyrrolecarbonylimino(N-methyl- 4,2-pyrrole)carbonylimino))bis(3,5-naphthalendisulfonic acid);

7,7'-(carbonyl-bis(imino-N-methyl-4,2-pyrrolecarbonylimino(N-methyl- 4,2-pyrrole)carbonylimino))bis(3,6-naphthalendisulfonic acid);

7,7'-(carbonyl-bis(imino-N-methyl-4,2-pyrrolecarbonylimino(N-methyl- 4,2-pyrrole)carbonylimino))bis(1,3,5-naphthalentrisulfonic acid);

8,8'-(carbonyl-bis(imino-N-methyl-4,2-pyrrolecarbonylimino(N-methyl- 4,2-pyrrole)carbonylimino))bis(1,3,6-naphthalentrisulfonic acid);

7,7'-(carbonyl-bis(imino-N-methyl-4,2-pyrrolecarbonylimino(N-methyl- 4,2-pyrrole)carbonylimino))bis(1,3-naphthalendisulfonic acid);

7,7'-(carbonyl-bis(imino-N-methyl-4,2-pyrrolecarbonylimino(N-methyl- 4,2-pyrrole)carbonylimino))bis(2,4-naphthalendisulfonic acid);

8,8'-(carbonyl-bis(imino-N-methyl-4,2-pyrrolecarbonylimino(N-methyl- 4,2-pyrrole)carbonylimino))bis(2,4-naphthalendisulfonic acid);

8,8'-(carbonyl-bis(imino-N-methyl-4,2-pyrrolecarbonylimino(N-methyl- 4,2-pyrrole)carbonylimino))bis(1,3,5-naphthalentrisulfonic acid);

8,8'-(carbonyl-bis(imino-N-methyl-4,2-pyrrolecarbonylimino(N-methyl- 4,2-pyrrole)carbonylimino))bis(5-naphthalensulfonic acid);

8,8'-(carbonyl-bis(imino-N-methyl-4,2-pyrrolecarbonylimino(N-methyl- 4,2 -pyrrole)carbonylimino))-bis(1,3-naphthalendisulfonic acid);

8,8'-(carbonyl-bis(imino-N-methyl-4,2-pyrrolecarbonylimino(N-methyl- 4,2-pyrrole)carbonylimino))bis(3,5-naphthalendisulfonic acid);

8,8'-(carbonyl-bis(imino-N-methyl-4,2-pyrrolecarbonylimino(N-methyl- 4,2-pyrrole)carbonylimino))bis(1,5-naphthalendisulfonic acid);

8,8'-(carbonyl-bis(imino-N-methyl-4,2-pyrrolecarbonylimino(N-methyl- 4,2-pyrrole) carbonylimino))bis(3-naphthalensulfonic acid);

8,8'-(carbonyl-bis(imino-N-methyl-4,2-pyrrolecarbonylimino(N-methyl- 4,2 -pyrrole)carbonylimino))bis(1-naphthalensulfonic acid);

2,2'-(carbonyl-bis(imino-N-methyl-4,2-pyrrolecarbonylimino(N-methyl- 4,2-pyrrole)carbonylimino))bis(1,5-naphthalendisulfonic acid);

7,7'-(carbonyl-bis(imino-N-methyl-4,2-pyrrolecarbonylimino(N-methyl- 4,2-pyrrole)carbonylimino))bis(1,6-naphthalendisulfonic acid);

7,7'-(carbonyl-bis(imino-N-methyl-4,2-pyrrolecarbonylimino(N-methyl- 4,2-pyrrole)carbonylimino))bis(2,6-naphthalendisulfonic acid);

7,7'-(carbonyl-bis(imino-N-methyl-4,2-pyrrolecarbonylimino(N-methyl- 4,2-pyrrole)carbonylimino))bis(1,5-naphthalendisulfonic acid);

7,7'-(carbonyl-bis(imino-N-methyl-4,2-pyrrolecarbonylimino(N-methyl- 4,2-pyrrole)carbonylimino))bis(2,5-naphthalendisulfonic acid);

7,7'-(carbonyl-bis(imino-N-methyl-4,2-pyrrolecarbonylimino(N-methyl- 4,2-pyrrole)carbonylimino))bis(2,3-naphthalendisulfonic acid);

8,8'-(carbonyl-bis(imino-N-methyl-4,2-pyrrolecarbonylimino(N-methyl- 4,2-pyrrole)carbonylimino))bis(1,6-naphthalendisulfonic acid);

8,8'-(carbonyl-bis(imino-N-methyl-4,2-pyrrolecarbonylimino(N-methyl- 4,2-pyrrole)carbonylimino))bis(2,6-naphthalendisulfonic acid);

8,8'-(carbonyl-bis(imino-N-methyl-4,2-pyrrolecarbonylimino(N-methyl- 4,2-pyrrole)carbonylimino))bis(2,5-naphthalendisulfonic acid);

8,8'-(carbonyl-bis(imino-N-methyl-4,2-pyrrolecarbonylimino(N-methyl- 4,2-pyrrole)carbonylimino))bis(3,6-naphthalendisulfonic acid);

8,8'-(carbonyl-bis(imino-N-methyl-4,2-pyrrolecarbonylimino(N-methyl- 4,2-pyrrole)carbonylimino))bis(2,3,5-naphthalentrisulfonic acid);

8,8'-(carbonyl-bis(imino-N-methyl-4,2-pyrrolecarbonylimino(N-methyl- 4,2-pyrrole)carbonylimino))bis(1,4,6-naphthalentrisulfonic acid);

8,8'-(carbonyl-bis(imino-N-methyl-4,2-pyrrolecarbonylimino(N-methyl- 4,2-pyrrole)carbonylimino))bis(2,4,6-naphthalentrisulfonic acid);

7,7'-(carbonyl-bis(imino-N-methyl-4,2-pyrrolecarbonylimino(N-methyl- 4,2-pyrrole)carbonylimino))bis(1-naphthalensulfonic acid);

7,7'-(carbonyl-bis(imino-N-methyl-4,2-pyrrolecarbonylimino(N-methyl- 4,2-pyrrole)carbonylimino))bis(2-naphthalensulfonic acid);

7,7'-(carbonyl-bis(imino-N-methyl-4,2-pyrrolecarbonylimino(N-methyl- 4,2 -pyrrole)carbonylimino))bis(3-naphthalensulfonic acid);

7,7'-(carbonyl-bis(imino-N-methyl-4,2-pyrrolecarbonylimino(N-methyl- 4,2-pyrrole) carbonylimino))bis(4-naphthalensulfonic acid);

7,7'-(carbonyl-bis(imino-N-methyl-4,2-pyrrolecarbonylimino(N-methyl- 4,2-pyrrole)carbonylimino))bis(1,4,6-naphthalentrisulfonic acid);

7,7'-(carbonyl-bis(imino-N-methyl-4,2-pyrrolecarbonylimino(N-methyl- 4,2-pyrrole)carbonylimino))bis(1,3,6-naphthalentrisulfonic acid);

7,7'-(carbonyl-bis(imino-N-methyl-4,2-pyrrolecarbonylimino(N-methyl- 4,2-pyrrole)carbonylimino))bis(2,4,6-naphthalentrisulfonic acid);

7,7'-(carbonyl-bis(imino-N-methyl-4,2-pyrrolecarbonylimino(N-methyl- 4,2-pyrrole)carbonylimino))bis(2,3,5-naphthalentrisulfonic acid);

and the pharmaceutically acceptable salts thereof.

As stated above, the compounds of the invention have been found to be active as antimetastatic agents. Accordingly, they can be used in mammals, including humans, for preventing and/or treating the metastatic spread of tumors metastasizing to bone, e.g. those of the breast, lung, prostate, kidney and thyroid, to liver and/or lung, e.g. melanoma and carcinoma arising in the gastrointestinal tract, pancreas and gallbladder. The antimetastatic activity of the compounds used in the invention is proven for instance by the fact that a representative compound of formula (I), 2,2'-(carbonyl-bis(imino-N-methyl- 4,2-pyrrolecarbonyl-imino(N-methyl-4,2-pyrrole)carbonylimino))-bis(1,5-naphthalendisulfonic acid) (compound of formula (IA)), when administered i.v. to mice 48 hours before the injection of a tumoral cells suspension, provided the following inhibition activity data:

85% inhibition on lung metastasis by murine melanoma B16F10;

100% inhibition on lung metastasis by human sarcoma A375; and

82% inhibition on liver metastasis by murine reticulumsarcoma M5076.

In addition, the compound of formula (IA), internal code FCE 27266, was found to be active in inhibiting spontaneous lung metastasis (87%) on Lewis lung carcinoma when administered at 10 mg/kg i.p. for 17 days in mice.

The compounds of formula (I), or pharmaceutically acceptable salts thereof, can be administered by the usual routes, for example, parenterally, e.g. by intravenous injection or infusion, intramuscularly, subcutaneously, topically or orally, intravenous injection of infusion being preferred. The dosage depends on the age, weight and condition of the patient and on the administration route.

A suitable dosage for the compounds of formula (I), for example a compound of formula (IA), or pharmaceutically acceptable salts thereof, for administration to adult humans is from about 0.5 to about 300 mg per dose 1–4 times a day.

The pharmaceutical compositions used in the invention may comprise a compound of formula (I) or a pharmaceutically acceptable salt thereof, as the active substance, in association with one or more pharmaceutically acceptable excipients and/or carriers.

The pharmaceutical compositions are usually prepared following conventional methods and are administered in a pharmaceutically suitable form. For instance, solutions for intravenous injection or infusion may contain as carrier, for example, sterile water or, preferably, they may be in the form of sterile aqueous isotonic saline solutions.

Suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride.

In the form for topical application, e.g. creams, lotions or pastes for use in dermatological treatment, the active ingredient may be mixed with conventional oleoginous or emulsifying excipients.

The solid oral forms, e.g. tablets and capsules, may contain, together with the active compound, diluents, e.g. lactose, dextrose, saccharose, cellulose, corn starch and potato starch; lubricants, e.g. silica, talc, stearic acid, magnesium or calcium stearate, and/or polyethylene glycols; binding agents, e.g. starches, arabic gums, gelatin, methylcellulose, carboxymethyl cellulose, polyvinylpyrrolidone; disaggregating agents, e.g. a starch, alginic acid, alginates, sodium starch glycolate; effervescing mixtures; dyestuffs; sweeteners; wetting agents, for instance, lecithin, polysorbates, laurylsulphates; and in general, non-toxic and pharmacologically inactive substances used in pharmaceutical formulations. Said pharmaceutical preparations may be manufactured in a known manner, for example by means of mixing, granulating, tabletting, sugar-coating or film-coating processes.

The compounds of formula (I), or pharmaceutically acceptable salts thereof, may be used in a method of treatment of the above mentioned pathological conditions comprising both separate and substantially contemporaneous administration of a composition containing a compound of formula (I), or a pharmaceutically acceptable salt thereof, and a pharmaceutical composition containing a different pharmaceutically active agent, typically an antitumor agent.

Object of the present invention is also to provide products containing an antimetastatic agent of formula (I), as defined above, or a pharmaceutically acceptable salt thereof, and an antitumor agent as a combined preparation for simultaneous, separate or sequential use in preventing and/or treating metastatic spread of tumors.

Antitumor agents that can be formulated with a compound of formula (I), or a pharmaceutically acceptable salt thereof, or, alternatively, can be administered in a combined method of treatment are, e.g., doxorubicin, daunomycin, epirubicin, idarubicin, etoposide, fluorouracil, mephalan, cyclophosphamide, bleomycin, vinblastin and mitomycin or a mixture of two or more thereof.

The compounds of formula (I), or pharmaceutically acceptable salts thereof, can therefore be used in a treatment to ameliorate a cancer.

The present invention also provides the new ureido compound 2,2'-(carbonyl-bis(imino-N-methyl-4,2-pyrrolecarbonyl-imino(N-methyl- 4,2-pyrrole)carbonyl-imino))-bis(1,5-naphthalendisulfonic acid), which can be represented by formula (IA):

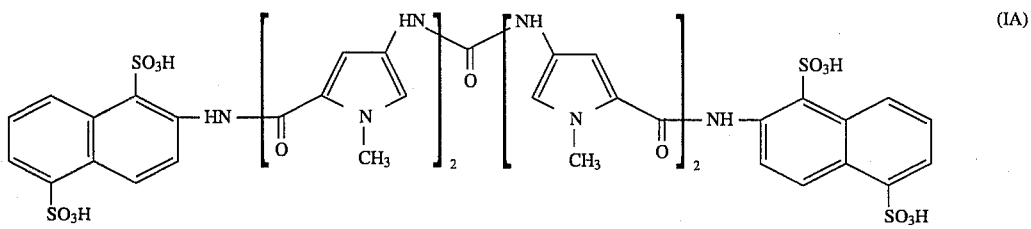

or a pharmaceutically acceptable salt thereof.

Typical examples of pharmaceutically acceptable salts of a compound of formula (IA) are those mentioned above in connection with the compounds of formula (I), the sodium and potassium salts being preferred.

The present invention also includes within its scope pharmaceutically acceptable bio-precursors (otherwise known as pro-drugs) of the compound of formula (IA), i.e. compounds which have a different formula to formula (I) above, but which nevertheless upon administration to a human being are converted directly or indirectly in vivo into the compound of formula (IA).

The new compound of formula (IA) is embraced by the general formula disclosed in WO 91/10649 but is not specifically mentioned therein. The compound of formula (IA) and the pharmaceutically acceptable salts thereof, besides being active as antimetastatic agents, are also angiogenesis inhibitors. Accordingly, they can be useful in treating several pathological conditions in mammals, including humans, where the growth of new blood vessels is detrimental, for example in chronic inflammation, diabetic retinopathy, psoriasis, rheumatoid arthritis and tumor growth.

Moreover, they are capable of neutralizing TNF-α and therefore can be employed in humans for prophylactic and/or therapeutic use in any disease state in which TNF-α is known to play a detrimental role. Typically such disease states are cachexia, septic shock, graft-versus-host disease, AIDS, cerebral malaria and rheumatoid arthritis.

Dosages and pharmaceutical compositions similar to those described above for the compounds of formula (I) can also be used for the compound of formula (IA) and the pharmaceutically acceptable salts thereof when it is administered to adult humans as an angiogenesis inhibitor and/or anti-TNF-α activity agent.

The present invention additionally provides a compound of formula (IA), or a pharmaceutically acceptable salt thereof, for use in a method of treatment of the human or animal body by therapy, in particular for use in preventing and/or treating the metastatic spread of tumors or for use as an angiogenesis inhibitor.

The present invention further provides a pharmaceutical composition comprising a pharmaceutically acceptable carrier and/or diluent and, as an active principle, the compound of formula (IA) or a pharmaceutically acceptable salt thereof.

The compound of formula (IA), and the salts thereof, can be prepared by a process comprising reacting a compound of formula (II)

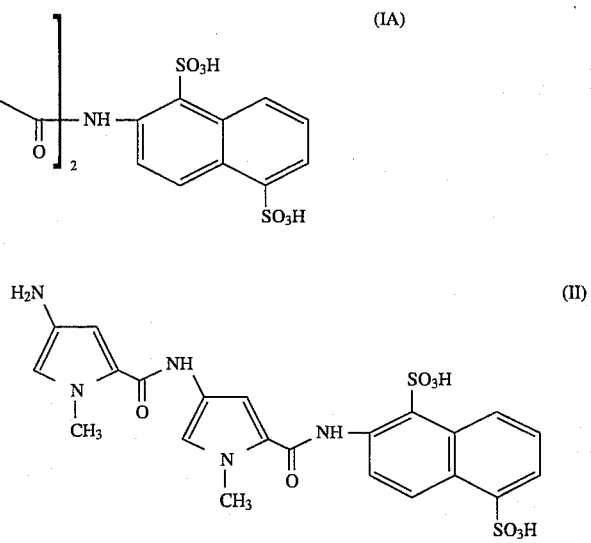

or a salt thereof, with a compound of formula (III)

wherein each of the X groups, which may be the same or different, is a leaving group, and if desired, salifying the compound of formula (IA) thus obtained; and/or, if desired, obtaining the free compound of formula (IA) from a salt thereof.

A salt of a compound of formula (II) may be a salt with inorganic bases, for example those mentioned above as pharmaceutically acceptable salts used in the invention, the sodium and potassium salts being the preferred.

Preferred examples of leaving groups, according to the meaning of X, are halogen atoms, in particular chlorine, or other easily displaceable groups such as imidazolyl, triazolyl, p-nitrophenoxy, trichlorophenoxy or trichloromethyloxy. The reaction of the compound of formula (II), or a salt thereof, with a compound of formula (III) is an analogy process and can be carried out according to well known methods; for example according to the conditions described in organic chemistry for this kind of reaction, i.e. for synthesis of urea derivatives.

Preferably, when in a compound of formula (III) X is a halogen atom, e.g. chlorine, the reaction may be carried out at a molar ratio of compound (II), or a salt thereof: compound (III) from about 1.1 to about 1.4. The reaction is preferably performed in organic solvents such as dimethylsulphoxide, hexamethylphosphotriamide, dimethylacetamide or, preferably, dimethylformamide, or their aqueous mixtures, or in water/dioxane or water/toluene mixtures, in the presence of either an organic base such as triethylamine or diisopropylethylamine, or an inorganic base such as sodium bicarbonate or sodium acetate. The reaction temperature may vary from about $-10°$ C. to about $50°$ C. and the reaction time from about 1 to about 12 hours. The compound of formula (IA) prepared according to the above described procedures may be purified by conventional methods such as by silica gel or alumina column chromatography, and/or by recrystallization from organic solvents such as lower aliphatic alcohols or dimethylformamide.

Analogously, salification of the compound of formula (IA) can be carried out by known methods in the art. The present invention further provides the compound of formula (II) or a salt thereof.

The compound of formula (II) may be obtained according to known procedures, for instance as described in WO 91/10649.

The compounds of formula (I) and the pharmaceutically acceptable salts thereof can be obtained according to WO 91/10649, for instance by following a procedure similar to that described above in connection with the preparation of a compound of formula (IA) and the pharmaceutically acceptable salts thereof.

The following examples further illustrate but do not limit the present invention:

EXAMPLE 1

2,2'-(carbonyl-bis(imino-N-methyl-4,2-pyrrolecarbonylimino(N-methyl- 4,2-pyrrole)carbonyl-imino))bis(1,5-naphthalendisulfonic acid)tetra sodium salt.

To a solution of 2-(amino-N-methyl-4,2-pyrrolecarbonylimino(N-methyl- 4,2-pyrrole)carbonylimino)) (1,5-naphthalendisulfonic acid) disodium salt hydrochloride (1256 mg, 2 mmols) in water (60 ml) and dioxane (20 ml), NaOH 1N (2 ml) and sodium acetate (328 mg, 4 mmols) was added under stirring.

The whole was cooled to $5°$ C. with an ice bath, then a solution of bis(trichloromethyl)carbonate (149 mg, 0.5 mmols) in dioxane (15 ml) was added dropwise in an hour. The mixture was stirred for 2 hours at room temperature. The solvents were evaporated under vacuum and the residue was chromatographed on a silica gel column with methylene chloride : methanol : water (300:200:20) as eluant, affording 856 mg of the title compound.

N.M.R. (DM $\delta$O-$d_6$): 3.85 (3H, s); 3.91 (3H, s); 6.90 (1H, d, J=1.8); 6.98 (1H, d, J=1.8); 7.09 (1H, d, J=1.8); 7.35 (1H, dd, J=7, J=8.8); 7.47 (1H, d, J=1.8); 7.9 (1H, d, J=7); 9.15 (1H, bs); 8.67–8.82 (2H, dd, J=9.6); 8.99 (1H, d, J=8.8); 9.98 (1H, bs); 12.64 (1H, bs).

F.A.B. M.S.: m/z 1207, [M−H]$^-$; 1185, [M−23]$^-$; 1105 (M−SO$_3$Na)$^-$.

U.V. (H$_2$O): $\lambda$ max 298; $E_1$ $_{cm}^1$ 522

By proceeding analogously, the following compounds can be prepared:

7,7'-(carbonyl-bis(imino-N-methyl-4,2-pyrrolecarbonylimino(N-methyl- 4,2-pyrrole)carbonylimino))bis(3,5-naphthalendisulfonic acid) tetrasodium salt;

N.M.R. (DMSO-$d_6$): $\delta$3.85 (3H,s); 3.90 (3H,s); 6.81 (1H, d, J=1.8); 6.90 (1H, d, J=1.8); 7.12 (1H,d,J=1.8); 7.32 (1H, d, J=1.8); 7.70 (1H, dd, J=1.6, J=8.6); 7.80 (1H, d, J=8.6); 8.11 (1H, d, J=1.6); 8.15 (1H, bs ), 8.58 (1H, d, J=1.7); 8.78 (1H, d, J=1.7); 10.05 (1H, bs); 10.94 (1H, bs).

F.A.B. M.S. m/z: 1209, M$^+$+H; 1187, M$^+$−Ne+H;

U.V. (H$_2$O) n.m.: $\lambda$ max ($E_1$ $_{cm}^{1\%}$): 321 (416); 231 (721).

7,7'-(carbonyl-bis(imino-N-methyl-4,2-pyrrolecarbonylimino(N-methyl- 4,2-pyrrole)carbonylimino))bis(3,6-naphthalendisulfonic acid) tetrasodium salt;

N.M.R. (DMSO-$d_6$): $\delta$3.85 (3H,s); 3.93 (3H,s); 6.81 (1H, d, J=1.8); 6.91 (1H, d, J=1.8); 7.08 (1H, d, J=1.8); 7.51 (1H, d, J=1.8); 7.68 (1H, dd, J=1.6, J=8.6); 7.78 (1H, d, J=8.6); 8.04 (1H, s); 8.12 (1H, bs); 8.23 (1H, s); 8.89 (1H, s); 10.02 (1H, bs); 10.98 (1H, bs);

F.A.B. M.S. m/z: 1209, M$^+$+H; 1187, M$^+$−Ne+H;

U.V. (H$_2$O) n.m.: $\lambda$ max ($E_1$ $_{cm}^{1\%}$): 323.4 (540); 227.7 (732).

7,7'-(carbonyl-bis(imino-N-methyl-4,2-pyrrolecarbonylimino(N-methyl- 4,2-pyrrole)carbonylimino))bis(1,3,5-naphthalentrisulfonic acid) hexasodium salt;

N.M.R. (DMSO-$d_6$): $\delta$3.85 (3H, s); 3.89 (3H, s); 6.78 (1H, d, J=1.8); 7.08 (1H, d, J=1.8); 7.22 (1H, d, J=1.8); 7.35 (1H, d, J=1.8); 8.25 (1H, d, J=1.9); 8.30 (1H, bs); 8.36 (1H, bs); 9.00 (1H, bs); 9.07 (1H, d, J=1.6); 9.82 (1H, bs); 10.20 (1H, bs);

U.V. (H$_2$O) n.m.: $\lambda$ max ($E_1$ $_{cm}^{1\%}$): 320 (374); 254 (444).

8,8'-(carbonyl-bis(imino-N-methyl-4,2-pyrrolecarbonylimino(N-methyl- 4,2-pyrrole)carbonylimino))bis(1,3,6-naphthalentrisulfonic acid); hexasodium salt;

N.M.R. (DMSO-$d_6$): $\delta$3.84 (3H, s); 3.88 (3H, s); 6.81 (1H, d, J=1.8); 7.07 (1H, d, J=1.8); 7.11 (1H, d, J=1.8); 7.42 (1H, d, J=1.8); 7.87 (1H, d, J=1.9); 7.87 (1H, d, J=1.9); 8.06 (1H, d, J=1.9); 8.12 (1H, bs); 8.33 (1H, d, J=1.9); 8.54 (1H, d, J=1.9); 9.93 (1H, bs); 12.19 (1H, bs).

U.V. (H$_2$O) n.m.: $\lambda$ max ($E_1$ $_{cm}^{1\%}$): 320 (374); 254 (444).

7,7'-(carbonyl-bis(imino-N-methyl-4,2-pyrrolecarbonylimino(N-methyl- 4,2-pyrrole)carbonylimino))bis(1,3-naphthalendisulfonic acid); tetrapotassium salt.

I.R. (KBr) cm$^{-1}$: 3450 (b); 1650; 1580; 1530; 1190; 1030;

N.M.R. (DMSO-$d_6$): $\delta$3.84 (3H, s); 3.87 (3H, s); 6.80 (1H, d); 7.05 (1H, d; 7.18 (1H, d); 7.33 (1H, d); 7.86 (2H, m); 8.00 (1H, d,); 8.16 (1H, bs); 8.21 (1H, d); 8.95 (1H, bs); 9.86 (1H, bs); 10.21 (1H, bs).

U.V. (H$_2$O) n.m.: $\lambda$ max ($E_1$ $_{cm}^{1\%}$): 316.8 (371); 248.95 (444)

F.A.B. M.J. m/z: 1273 (M$^+$+H); 1311 ((M$^+$+K)

7,7'-(carbonyl-bis(imino-N-methyl-4,2-pyrrolecarbonylimino(N-methyl- 4,2-pyrrole)carbonylimino))bis(2,4-naphthalendisulfonic acid) tetrasodium salt;

N.M.R. (DMSO-$d_6$): $\delta$3.85 (3H, s); 3.89 (3H, s); 6.81 (1H, d, J=1.7); 7.06 (1H, d, J=1.7); 7.22 (1H, d, J=1.7); 7.33 (1H, d, J=1.7); 7.33 (1H, d, J=1.7); 7.38 (1H, dd, J=2.0, J=9.5); 7.92 (1H, bs); 8.10 (1H, d, J=1.7); 8.20 (1H, bs); 8.32 (1H, d, J=2.0); 8.69 (1H, d, J=9.4); 9.88 (1H, bs ); 10.08 (1H, bs).

8,8'-(carbonyl-bis(imino-N-methyl-4,2-pyrrolecarbonylimino(N-methyl- 4,2-pyrrole)carbonylimino))bis(2,4-naphthalendisulfonic acid); tetrasodium salt;

N.M.R. (DMSO-$d_6$): $\delta$3.85 (6H, s); 6.81 (1H, d, J=1.7 Hz); 7.06 (1H, d, J=1+Hz); 7.25 (1H, d, J=1.7 Hz); 7.34 (1H, d, J=1.7 Hz); 7.4÷7.6 (2H, m); 8.14 (1H, bs); 8.25 (2H, s); 8.73 (1H, dd, J=13 Hz, J=8.3 Hz); 9.92 (1H, bs); 10.07 (1H, bs).

U.V. (H$_2$) n.m.: $\lambda$ max ($E_1$ $_{cm}^{1\%}$): 307 (435); 231 (932).

F.A.B. m/z : 1209 (M$^+$+1); 1231 (M$^+$+Ne); 1128 (M$^+$−SO$_3$)

8,8'-(carbonyl-bis(imino-N-methyl-4,2-pyrrolecarbonylimino(N-methyl- 4,2-pyrrole)carbonylimino))bis(1,3,5-naphthalentrisulfonic acid) hexasodium salt;

I.R. (KBr) cm$^{-1}$: 3440 , 1640, 1590, 1190, 1030

N.M.R. (DMSO-$d_6$): $\delta$3.80 (3H, s); 3.83 (3H, s); 6.80 (1H, d); 7.06 (2H, m); 7.40 (1H, d); 7.88 (1H, d); 7.99 (1H, d); 8.02 (1H, bs); 8.57 (1H, d); 9.33 (1H, d); 9.91 (1H, bs); 12.29 (1H, bs).

U.V. (H$_2$) nm: λ max (E$_1$ $_{cm}$$^{1\%}$): 311 (266); 233 (551)
F.A.B.-M.S. m/z : 1411, M$^-$–H;1389, M$^-$–Na
8,8'-(carbonyl-bis(imino-N-methyl-4,2-pyrrolecarbonylimino(N-methyl- 4,2-pyrrole)carbonylimino))bis(5-naphthalensulfonic acid) disodium salt;

N.M.R. (DMSO-d$_6$): δ3.85 (6H, s); 6.84 (1H, d, J=1.8); 7.05 (1H, d, J=1.8); 7.25 (1H, d, J=1.8); 7.35 (1H, d, J=1.8); 7.46–7.56 (3H, m); 7.92–8.00 (2H, m); 8.15 (1H, bs); 8.87 (1H, 9.89 (1H, bs); 10.03 (1H, bs);

U.V. (H$_2$O) n.m.: λ max (E$_1$ $_{cm}$$^{1\%}$) : 310 (531); 227 (1043)
F.A.B. M.S. m/z: 1005, (M$^+$+H); 1027 (M$^+$+Ne); 512.
8,8'-(carbonyl-bis(imino-N-methyl-4,2-pyrrolecarbonylimino(N-methyl- 4,2-pyrrole)carbonylimino))bis(1,3-naphthalendisulfonic acid) tetrasodium salt;

N.M.R. (DMSO-d$_6$): δ3.84 (3H, s); 3.86 (3H, s); 6.81 (1H, d, J=1.8); 7.08 (1H, bs); 7.41 1H, d, J=1.8); 7.50 (1H, t, J=7.0); 7.78 (1H, d, J=7.0); 8.02 (1H, d, J=7.0); 8.11 (2H, m); 8.53 (1H, d, J=2.02); 9.93 (1H, bs); 12.21 (1H, bs);

U.V. (H$_2$O) n.m.: λ max (E$^1$ $^{cm1\%}$): 309.05 (403); 229.65, 735

F.A.B. M.S. m/z :1209, M$^+$+H; 1231, M$^+$+Ne; 1187, M$^+$–Ne+H; 1129; 640; 618; 614; 592.
8,8'-(carbonyl-bis(imino-N-methyl-4,2-pyrrolecarbonylimino(N-methyl- 4,2-pyrrole)carbonylimino))bis(3,5-naphthalendisulfonic acid) tetrasodium salt;

N.M.R. (DMSO-d$_6$): δ3.85 (6H, s); 6.83 (1H, d, J=1.8); 7.06 (1H, d, J=1.8); 7.26 (1H, d, J=1.8); 7.38 (1H, d, J=1.08); 7.50 (1H, d, J=7.8); 7.72 (1H, dd, J=1.7, J=8.9); 7.98 (1H, d, J=7.8); 8.25 (1H, bs); 9.19 (1H, d, J=1.7); 9.91 (1H, bs); 10.03 (1H, bs);

U.V. (H$_2$O) n.m.: λ max (E$_1$ $_{cm}$$^{1\%}$): 310 (431); 231 (1027)
F.A.B. M.S. m/z: 1209, M$^+$+H; 640; 618; 614; 592;
8,8'-(carbonyl-bis(imino-N-methyl-4,2-pyrrolecarbonylimino(N-methyl- 4,2-pyrrole)carbonylimino))bis(1,5-naphthalendisulfonic acid) tetrasodium salt;

I.R. (KBr) cm$^{-1}$: 3440b, 1660, 1640, 1585, 1180, 1030.
N.M.R. (DMSO-d$_6$): δ3.84 (3H, s); 3.85 (3H, s); 6.80 (1H, d); 7.07 (2H, m); 7.41 (2H, m); 7.92 (2H, dd); 8.12 (1.12, 1H, s); 8.27 (1H, dd); 9.07 (1H, dd); 9.90 (1H, bs); 12.27 (1H, bs).

U.V. (H$_2$O) n.m.: λ max (E$_1$ $_{cm}$$^{1\%}$) : 316 (331); 229 (478)
F.A.B. M.S. m/z : 1209, M$^+$+1; 1231, M$^+$+23; 1128, M–80
8,8'-(carbonyl-bis(imino-N-methyl-4,2-pyrrolecarbonylimino(N-methyl- 4,2-pyrrole)carbonylimino))bis(3-naphthalensulfonic acid) disodium salt;

I.R. (KBr) cm$^{-1}$: 3430 b, 1640, 1585, 1200, 1030
N.M.R. (DMSO-d$_6$): δ3.84 (6H, s); 6.86 (1H, d); 7.05 (1H, d); 7.24 (1H, d); 7.35 (1H, d) 7.54 (2H, m); 7.70 (1H, dd); 7.90 (2H, m); 8.15 (1H, d); 8.15 (1H, d); 8.95 (1H, bs); 9.94 (1H, bs); 10.03 (1H, bs).

U.V. (H$_2$O) n.m: λ max (E$_1$ $_{cm}$$^{1\%}$): 304 (366); 226 (1002)
F.A.B. M.S. m/z: 1005, M$^+$+H; 1027, M$^+$+2Na
8,8'-(carbonyl-bis(imino-N-methyl-4,2-pyrrolecarbonylimino(N-methyl- 4,2-pyrrole)carbonylimino))bis(1-naphthalensulfonic acid) disodium salt;

N.M.R. (DMSO-d$_6$): δ3.84 (3H, s); 3.85 (3H, s); 6.82 (1H, d, J=1.8); 7.06 (1H, d, J=1.8); 7.09 (1H, d, J=1.8); 7.39–7.54 (3H, m); 7.74 (1H, dd, J=1.3, J=0.3, J=8.2); 7.93–8.02 (2H, m); 8.13 (1H, bs); 8.26 (1H, dd, J=1.5, J=7.3); 9.93 (1H, bs); 12.20 (1H, bs);

F.A.B. M.S. m/z: 1005, M$^+$+H; 1027,M$^+$+Ne;
U.V. (H$_2$O) n.m.: λ max (E$_1$ $_{cm}$$^{1\%}$): 312 (490); 224 (831)
7,7'-(carbonyl-bis(imino-N-methyl-4,2-pyrrolecarbonylimino(N-methyl- 4,2-pyrrole )carbonylimino))bis(1,6-naphthalendisulfonic acid) tetrasodium salt;
7,7'-(carbonyl-bis(imino-N-methyl-4,2-pyrrolecarbonylimino(N-methyl- 4,2-pyrrole)carbonylimino))bis(2,6-naphthalendisulfonic acid) tetrasodium salt;
7,7'-(carbonyl-bis(imino-N-methyl-4,2-pyrrolecarbonylimino(N-methyl- 4,2-pyrrole)carbonylimino))bis(1,5-naphthalendisulfonic acid) tetrasodium salt;
7,7'-(carbonyl-bis(imino-N-methyl-4,2-pyrrolecarbonylimino(N-methyl- 4,2-pyrrole)carbonylimino))bis(2,5-naphthalendisulfonic acid) tetrasodium salt;
7,7'-(carbonyl-bis(imino-N-methyl-4,2-pyrrolecarbonylimino(N-methyl- 4,2-pyrrole)carbonylimino))bis(2,3-naphthalendisulfonic acid) tetrasodium salt;
8,8'-(carbonyl-bis(imino-N-methyl-4,2-pyrrolecarbonylimino(N-methyl- 4,2-pyrrole)carbonylimino))bis(1,6-naphthalendisulfonic acid) tetrasodium salt;
8,8'-(carbonyl-bis(imino-N-methyl-4,2-pyrrolecarbonylimino(N-methyl- 4,2-pyrrole)carbonylimino))bis(2,6-naphthalendisulfonic acid) tetrasodium salt;
8,8'-(carbonyl-bis(imino-N-methyl-4,2-pyrrolecarbonylimino(N-methyl- 4,2-pyrrole)carbonylimino))bis(2,5-naphthalendisulfonic acid) tetrasodium salt;
8,8'-(carbonyl-bis(imino-N-methyl-4,2-pyrrolecarbonylimino(N-methyl- 4,2-pyrrole)carbonylimino))bis(3,6-naphthalendisulfonic acid) tetrasodium salt;
8,8'-(carbonyl-bis(imino-N-methyl-4,2-pyrrolecarbonylimino(N-methyl- 4,2-pyrrole)carbonylimino))bis(2,3,5-naphthalentrisulfonic acid) hexasodium salt;
8,8'-(carbonyl-bis(imino-N-methyl-4,2-pyrrolecarbonylimino(N-methyl- 4,2-pyrrole)carbonylimino))bis(1,4,6-naphthalentrisulfonic acid) hexasodium salt;
8,8'-(carbonyl-bis(imino-N-methyl-4,2-pyrrolecarbonylimino(N-methyl- 4,2-pyrrole)carbonylimino))bis(2,4,6-naphthalentrisulfonic acid) hexasodium salt;
7,7'-(carbonyl-bis(imino-N-methyl-4,2-pyrrolecarbonylimino(N-methyl- 4,2-pyrrole)carbonylimino))bis(1-naphthalensulfonic acid) disodium salt;
7,7'-(carbonyl-bis(imino-N-methyl-4,2-pyrrolecarbonylimino(N-methyl- 4,2-pyrrole)carbonylimino))bis(2-naphthalensulfonic acid) disodium salt;
7,7'-(carbonyl-bis(imino-N-methyl-4,2-pyrrolecarbonylimino(N-methyl- 4,2-pyrrole)carbonylimino))bis(3-naphthalensulfonic acid) disodium salt;
7,7'-(carbonyl-bis(imino-N-methyl-4,2-pyrrolecarbonylimino(N-methyl- 4,2-pyrrole)carbonylimino))bis(4-naphthalensulfonic acid) disodium salt;
7,7'-(carbonyl-bis(imino-N-methyl-4,2-pyrrolecarbonylimino(N-methyl- 4,2-pyrrole)carbonylimino))bis(1,4,6-naphthalentrisulfonic acid) hexasodium salt;
7,7'-(carbonyl-bis(imino-N-methyl-4,2-pyrrolecarbonylimino(N-methyl- 4,2-pyrrole)carbonylimino))bis(1,3,6-naphthalentrisulfonic acid) hexasodium salt;
7,7'-(carbonyl-bis(imino-N-methyl-4,2-pyrrolecarbonylimino(N-methyl- 4,2-pyrrole)carbonylimino))bis(2,4,6-naphthalentrisulfonic acid) hexasodium salt; and
7,7'-(carbonyl-bis(imino-N-methyl-4,2-pyrrolecarbonylimino(N-methyl- 4,2-pyrrole)carbonylimino))bis(2,3,5-naphthalentrisulfonic acid) hexasodium salt.

EXAMPLE 2

2,2'-(carbonyl-bis(imino-N-methyl-4,2-pyrrolecarbonylimino(N-methyl- 4,2-pyrrole)carbonylimino))bis(1,5-naphthalenedisulfonic acid).

A solution of 2,2'-(carbonyl-bis(imino-N-methyl-4,2-pyrrolecarbonyl-imino(N-methyl- 4,2-pyrrole)carbonylimino-))bis(1,5-naphthalenedisulfonic acid)tetrasodium salt (400 mg) in water (10 ml), is chromatographed on an Amberlite IR-120(H) column (20 ml), with water as eluent.

The solution is evaporated to dryness in vacuum, affording 0.3 g of the title compound.

EXAMPLE 3

Intramuscular Injection 40 mg/ml

An injectable pharmaceutical preparation can be manufactured by dissolving 40 g of 2,2'-(carbonyl-bis(imino-N- methyl- 4,2-pyrrolecarbonyl-imino(N-methyl-4,2-pyrrole)carbonylimino))bis(1,5-naphthalenedisulfonic acid) tetrasodium salt in water for injection (1000 ml) and sealing ampoules of 1–10 ml.

We claim:

1. A method of inhibiting tumoral cell adhesion to lung, liver, or bone in mammals comprising administering to a mammal in need thereof a therapeutically effective amount of a compound of formula (I)

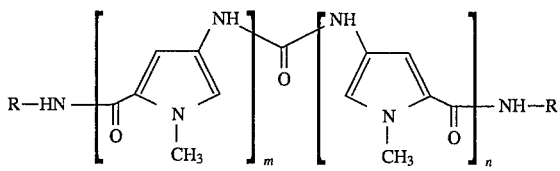

wherein
each of m and n, being the same, is an integer of 1 to 3; and each of the R groups, which are the same, is a naphthyl group substituted by 1 to 3 sulfonic groups, or a pharmaceutically acceptable salt thereof.

2. A method according to claim 1, wherein in the compound of formula (I), m and n are each 2.

3. A method according to claim 1, wherein the compound of formula (I) is selected from:

7,7'-(carbonyl-bis(imino-N-methyl-4,2-pyrrolecarbonylimino(N-methyl- 4,2-pyrrole)carbonyl-imino))bis(3,5-naphthalendisulfonic acid);

7,7'-(carbonyl-bis(imino-N-methyl-4,2-pyrrolecarbonylimino(N-methyl- 4,2-pyrrole)carbonylimino))bis(3,6-naphthalendisulfonic acid);

7,7'-(carbonyl-bis(imino-N-methyl-4,2-pyrrolecarbonylimino(N-methyl- 4,2-pyrrole)carbonylimino))bis(1,3,5-naphthalentrisulfonic acid);

8,8'-(carbonyl-bis(imino-N-methyl-4,2-pyrrolecarbonylimino(N-methyl- 4,2-pyrrole)carbonylimino))bis(1,3,6-naphthalentrisulfonic acid);

7,7'-(carbonyl-bis(imino-N-methyl-4,2-pyrrolecarbonylimino(N-methyl- 4,2-pyrrole)carbonylimino))bis(1,3-naphthalendisulfonic acid);

7,7'-(carbonyl-bis(imino-N-methyl-4,2-pyrrolecarbonylimino(N-methyl- 4,2-pyrrole)carbonylimino))bis(2,4-naphthalendisulfonic acid);

8,8'-(carbonyl-bis(imino-N-methyl-4,2-pyrrolecarbonylimino(N-methyl- 4,2-pyrrole)carbonylimino))bis(2,4-naphthalendisulfonic acid);

8,8'-(carbonyl-bis(imino-N-methyl-4,2-pyrrolecarbonylimino(N-methyl- 4,2-pyrrole)carbonylimino))bis(1,3,5-naphthalentrisulfonic acid);

8,8'-(carbonyl-bis(imino-N-methyl-4,2-pyrrolecarbonylimino(N-methyl- 4,2-pyrrole)carbonylimino))bis(5-naphthalensulfonic acid);

8,8'-(carbonyl-bis(imino-N-methyl-4,2-pyrrolecarbonylimino(N-methyl- 4,2-pyrrole)carbonylimino))bis(1,3-naphthalendisulfonic acid);

8,8'-(carbonyl-bis(imino-N-methyl-4,2-pyrrolecarbonylimino(N-methyl- 4,2-pyrrole)carbonylimino))bis(3,5-naphthalendisulfonic acid);

8,8'-(carbonyl-bis(imino-N-methyl-4,2-pyrrolecarbonylimino(N-methyl- 4,2-pyrrole)carbonylimino))bis(1,5-naphthalendisulfonic acid);

8,8'-(carbonyl-bis(imino-N-methyl-4,2-pyrrolecarbonylimino(N-methyl- 4,2-pyrrole)carbonylimino))bis(3-naphthalensulfonic acid);

8,8'-(carbonyl-bis(imino-N-methyl-4,2-pyrrolecarbonylimino(N-methyl- 4,2-pyrrole)carbonylimino))bis(1-naphthalensulfonic acid);

2,2'-(carbonyl-bis(imino-N-methyl-4,2-pyrrolecarbonylimino(N-methyl- 4,2-pyrrole)carbonylimino))bis(1,5-naphthalendisulfonic acid);

7,7'-(carbonyl-bis(imino-N-methyl-4,2-pyrrolecarbonylimino (N-methyl- 4,2-pyrrole)carbonylimino))bis(1,6-naphthalendisulfonic acid);

7,7'-(carbonyl-bis(imino-N-methyl-4,2-pyrrolecarbonylimino(N-methyl- 4,2-pyrrole)carbonylimino))bis(2,6-naphthalendisulfonic acid);

7,7'-(carbonyl-bis(imino-N-methyl-4,2-pyrrolecarbonylimino(N-methyl- 4,2-pyrrole)carbonylimino))bis(1,5-naphthalendisulfonic acid);

7,7'-(carbonyl-bis(imino-N-methyl-4,2-pyrrolecarbonylimino(N-methyl- 4,2-pyrrole)carbonylimino))bis(2,5-naphthalendisulfonic acid);

7,7'-(carbonyl-bis(imino-N-methyl-4,2-pyrrolecarbonylimino(N-methyl- 4,2-pyrrole)carbonylimino))bis(2,3-naphthalendisulfonic acid);

8,8'-(carbonyl-bis(imino-N-methyl-4,2-pyrrolecarbonylimino(N-methyl- 4,2-pyrrole)carbonylimino))bis(1,6-naphthalendisulfonic acid);

8,8'-(carbonyl-bis(imino-N-methyl-4,2-pyrrolecarbonylimino(N-methyl- 4,2-pyrrole)carbonylimino))bis(2,6-naphthalendisulfonic acid);

8,8'-(carbonyl-bis(imino-N-methyl-4,2-pyrrolecarbonylimino(N-methyl- 4,2-pyrrole)carbonylimino))bis(2,5-naphthalendisulfonic acid);

8,8'-(carbonyl-bis(imino-N-methyl-4,2-pyrrolecarbonylimino(N-methyl- 4,2-pyrrole)carbonylimino))bis(3,6-naphthalendisulfonic acid);

8,8'-(carbonyl-bis(imino-N-methyl-4,2-pyrrolecarbonylimino (N-methyl- 4,2-pyrrole)carbonylimino))bis(2,3,5-naphthalentrisulfonic acid);

8,8'-(carbonyl-bis(imino-N-methyl-4,2-pyrrolecarbonylimino(N-methyl- 4,2-pyrrole)carbonylimino))bis(1,4,6-naphthalentrisulfonic acid);

8,8'-(carbonyl-bis(imino-N-methyl-4,2-pyrrolecarbonylimino(N-methyl- 4,2-pyrrole)carbonylimino))bis(2,4,6-naphthalentrisulfonic acid);

7,7'-(carbonyl-bis(imino-N-methyl-4,2-pyrrolecarbonylimino (N-methyl- 4,2-pyrrole)carbonylimino))bis(1-naphthalensulfonic acid);

7,7'-(carbonyl-bis(imino-N-methyl-4,2-pyrrolecarbonylimino(N-methyl- 4,2-pyrrole)carbonylimino))bis(2-naphthalensulfonic acid);

7,7'-(carbonyl-bis(imino-N-methyl-4,2-pyrrolecarbonylimino(N-methyl- 4,2-pyrrole)carbonylimino))bis(3-naphthalensulfonic acid);

7,7'-(carbonyl-bis(imino-N-methyl-4,2-pyrrolecarbonylimino(N-methyl- 4,2-pyrrole)carbonylimino))bis(4-naphthalensulfonic acid);

7,7'-(carbonyl-bis(imino-N-methyl-4,2-pyrrolecarbonylimino(N-methyl- 4,2-pyrrole)carbonylimino))bis(1,4,6-naphthalentrisulfonic acid);

7,7'-(carbonyl-bis(imino-N-methyl-4,2-pyrrolecarbonylimino(N-methyl- 4,2-pyrrole)carbonylimino))bis(1,3,6-naphthalentrisulfonic acid);

7,7'-(carbonyl-bis(imino-N-methyl-4,2-pyrrolecarbonylimino(N-methyl- 4,2-pyrrole)carbonylimino))bis(2,4,6-naphthalentrisulfonic acid); or 7,7'-(carbonyl-bis(imino-N-methyl-4,2-pyrrolecarbonylimino(N-methyl- 4,2-pyrrole)carbonylimino))bis(2,3,5-naphthalentrisulfonic acid);

or a pharmaceutically acceptable salt thereof.

4. A method of inhibiting tumoral cell adhesion to lung, liver, or bone in mammals comprising both separate and substantially contemporaneous administration to a mammal in need thereof of a composition containing a compound of formula (I), or a pharmaceutically acceptable salt thereof, as defined in claim 1, and a pharmaceutical composition containing an antitumor agent.

5. 2,2'-(carbonyl-bis(imino-N-methyl-4,2-pyrrolecarbonylimino(N-methyl- 4,2-pyrrole)carbonylimino))bis(1,5-naphthalenedisulfonic acid) of formula (IA)

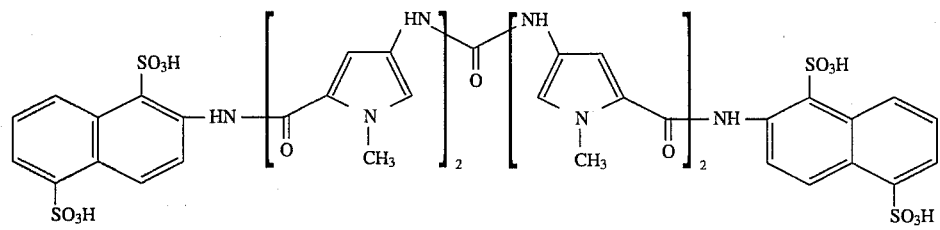

(IA)

or a pharmaceutically acceptable salt thereof.

6. A pharmaceutical composition comprising a pharmaceutically acceptable carrier and/or diluent and, as an active principle, the compound of formula (IA) as defined in claim 5 or a pharmaceutically acceptable salt thereof.

7. A method of inhibiting tumoral cell adhesion to lung, liver, or bone in mammals comprising administering to a mammal in need thereof a therapeutically effective amount of the compound 2,2'-(carbonyl-bis(imino-N-methyl-4,2-pyrrolecarbonyl-imino(N-methyl- 4,2-pyrrole)carbonylimino))-bis(1,5-naphthalenedisulfonic acid) or a pharmaceutically acceptable salt thereof.

* * * * *

UNITED STATES PATENT AND TRADEMARK OFFICE
CERTIFICATE OF CORRECTION

PATENT NO. : 5,534,539
DATED : July 9, 1996
INVENTOR(S) : Nicola MONGELLI, et al.

It is certified that error appears in the above-indentified patent and that said Letters Patent is hereby corrected as shown below:

On the title page, Item [54], and in Column 1, the title should read:

--BIOLOGICALLY ACTIVE UREIDO DERIVATIVES USEFUL AS ANTI-METASTATIC AGENTS--

Also, in Item [75], the fourth inventor's place of residence should read:

--Seregno--

Signed and Sealed this

Fifth Day of November, 1996

Attest:

BRUCE LEHMAN

Attesting Officer        Commissioner of Patents and Trademarks